United States Patent [19]

Epstein et al.

[11] 4,083,692

[45] Apr. 11, 1978

[54] DETECTION AND ESTIMATION OF MICROQUANTITIES OF ALKYLATING AGENTS

[75] Inventors: Joseph Epstein, Baltimore, Md.; Robert M. Heggie; John J. Norman, both of Ottawa, Canada

[73] Assignee: The United States of America as represented by the Secretary of the Army, Washington, D.C.

[21] Appl. No.: 57,410

[22] Filed: Jun. 4, 1970

[51] Int. Cl.[2] .............................................. G01N 31/22

[52] U.S. Cl. ................................ 23/232 R; 23/230 R; 252/408; 260/924; 260/934

[58] Field of Search .................. 23/230, 232; 252/408; 260/924, 295, 934, 944, 945

[56] References Cited

U.S. PATENT DOCUMENTS

| | | | |
|---|---|---|---|
| 2,911,430 | 11/1959 | Fitch | 260/945 |
| 2,919,977 | 1/1960 | Grant | 23/230 |
| 2,980,581 | 4/1961 | Schrader | 260/945 X |
| 3,049,411 | 8/1962 | Gelman et al. | 23/232 |
| 3,082,240 | 3/1963 | Lorenz et al. | 260/945 X |
| 3,309,371 | 3/1967 | Curry et al. | 260/925 |
| 3,451,901 | 6/1969 | Seiger et al. | 23/232 X |

*Primary Examiner*—Richard E. Schafer

*Attorney, Agent, or Firm*—Nathan Edelberg; Robert W. Church

[57] ABSTRACT

A method comprising an unknown solution adding an organophosphorus thio acid salt solution for sufficient time to form compounds having anticholinesterase activity in the reaction solution, contacting the reaction solution with a cholinesterase supported on a suitable substrate, adding indoxyl acetate and observing a non-color or blue color change in the substrate; the absence of color indicates the formation of compounds with anticholinesterase activity and the blue color of the substrate indicating that there was no formation of compounds with anticholinesterase activity.

5 Claims, No Drawings

DETECTION AND ESTIMATION OF MICROQUANTITIES OF ALKYLATING AGENTS

DEDICATORY CLAUSE

The invention described herein may be manufactured, used, and licensed for the Government for governmental purposes without the payment to us of any royalty thereon.

This invention is directed to the process of detecting sulfur and nitrogen mustards by their reaction with organophosphorus thio acid salts forming novel compounds with anticholinesterase activity.

An object of this invention is to detect sulfur and nitrogen mustards at lower concentrations than have been previously possible, thus enabling safe human consumption of the aqueous system.

The prior art methods for detecting mustard agents in an aqueous media are operative at concentrations between 10–40 ppm. Malatesta et al, 11 Farmaco (Pavia) Ed. Sci. 10, 257 (1955) disclose the potentiometric titration of chloride ion liberated on hydrolysis. Epstein et al, Anal Chem 27, 1435 (1955) disclose a method based upon the production of a colored product to indicate the presence of mustard agents. Trams, Anal Chem. 30, 256 (1958) proposes a method based upon the formation of a complex which is utilized for the detection of the mustard agent.

The above-mentioned prior art methods were not of sufficient sensitivity for our purpose.

An investigation was instituted to seek new avenues for detecting nitrogen and sulfur mustards by a single procedure at a level of detection between 1 - 2 parts per million. There has been no single method available that permits the modification of both sulfur and nitrogen mustards forming a compound possessing anticholinesterase in view of the fact that it has been known that nitrogen mustard will inhibit cholinesterase as distinguished from sulfur mustard which will not inhibit cholinesterase.

Now for the first time there is a method permitting the detection of mustard agents of a level of concentration, i.e. 2 parts per million or less, in an aqueous system. Thus, if a water sample tested negative by this test, it would be safe for human consumption.

At ambient conditions a test sample medium of about 25 microliters suspected of containing mustard agents is added to an aqueous solution of an O-alkyl alkylphosphonothioate salt forming a reaction solution which is permitted to stand for about 7.5 to 15 minutes, sufficient time to form anticholinesterase active compounds if the mustard agents were originally present in the test sample. Enzyme paper is moistened with the reaction solution at a temperature between 15° to 35° C and allowed to stand for about 7.5 to 15 minutes then adding an indoxyl acetate tablet which is crushed with subsequent shaking of the solution and permitted to stand for about 10 to 15 minutes. The enzyme paper is observed for the absence or appearance of a blue color during the 10 to 15 minute interval thus indicating the presence or absence of enzyme activity. If no anticholinesterase has formed, the enzyme will not be inhibited and thus the enzyme paper will become a blue color indicating no mustard agent present in the test sample for the formation of the anticholinesterase active compounds. For a positive result indicating the formation of compounds with anticholinesterase activity, the color of the enzyme paper will be unchanged thus showing the presence of about 0.5 to 2.0 parts per million or greater of mustard agent present in the test sample. The general scheme of the described method is summarized as follows:

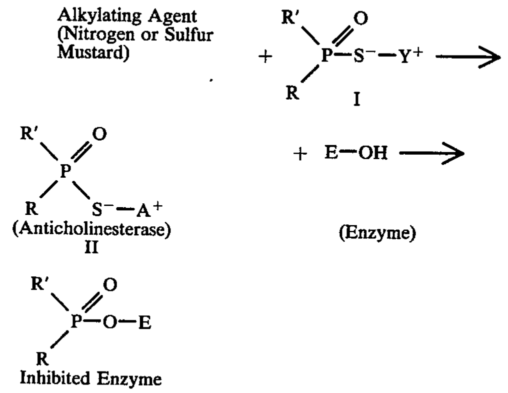

Wherein:

Alkylating agent may be:

bis-(2-chloroethyl)-sulfide
2,2'-bis-(2"-chloroethylthio)-diethylether
1,2-bis-(2'-chloroethylthio)-ethane
tris -(2-chloroethyl)-amine
bis -(2-chloroethyl)-ethylamine
bis -(2-chloroethyl)-methylamine R is alkoxy groups from $C_1$ to $C_5$ carbon atoms R' is alkyl groups or alkoxy groups from $C_1$ to $C_5$ carbon atoms.

A is:

(a) $-C_2H_4-S-C_2H_4-Cl$ (b) $-C_2H_4-S-C_2H_4-O-C_2H_4-S-C_2H_4-Cl$ (c) $-C_2H_4-S-C_2H_4-S-C_2H_4-Cl$ (d)

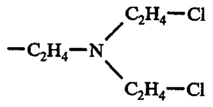

(e)

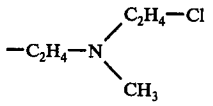

(f)

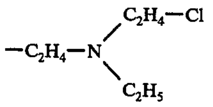

Y is: Na, K, $(Z)_4\overset{+}{N}$, $(Q)_4\overset{+}{N}$, $(Z_{1-3}-Q_{1-3})_4\overset{+}{N}$,

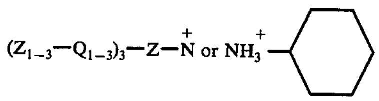

Wherein:

Z is $C_1$ to $C_4$ carbon atoms

Q is aryl for example phenyl, or alkyl substituted aryl for example, toluene.

The concentration of the O-alkyl alkylphosphonothioate salt is in the range between $6.5 \times 10^{-5}$ M to $3.2 \times 10^{-5}$ M in a 10 ml aliquot. We have concluded that with the increasing chain length from ethyl to amyl in the alkoxy portion of the salt a smaller concentration is required for the coupling reaction forming the anticholinesterase active compound and does not adversely effect the enzyme system in the method of this invention. The cation portion of the salt exemplified by Y in Formula I does not effect the sensitivity of the testing system.

The suspected testing sample should have a pH between 6 and 9.

EXAMPLE 1

(a) An aqueous solution comprising about 25 microliters or less of a mustard member selected from the group consisting of bis-(2-chloroethyl)-sulfide, 2,2'-bis-(2''-chloroethylthio)-diethylether, 1,2-bis-(2'-chloroethylthio)-ethane, tris (2-chloroethyl)-amine, bis-(2-chloroethyl)-ethylamine, and bis-(2-chloroethyl)-methylamine in a concentration range between 2 to 0.5 parts per million in a solvent, dimethyl-formamide or dioxane, was added to 10 ml aqueous solution including about $3.5 \times 10^{-5}$ to $6.5 \times 10^{-5}$ molar of O-alkyl alkylphosphonothioate salt and standing for a time between 7.5 to 15 minutes forming anticholinesterase active compounds. Contacting an enzymatic paper comprising bovine erythrocyte acetylcholinesterase with the anticholinesterase active solution at a temperature between 15° to 35° C for a time between 7.5 to 15 minutes to inhibit the acetylcholinesterase and then adding a tablet comprising indoxyl acetate and buffer with subsequent shaking and standing for a time interval between 10 to 15 minutes, the color of the paper is unchanged indicating a range of 2 to 0.5 parts per million of mustard agent present in the test sample.

(b) Results intermediate between 2 to 0.5 parts per million are obtained with a time and temperature occurring between the limits set forth in (a) above.

EXAMPLE 2

(a) An aqueous solution comprising about 25 microliters including about 2 ppm (parts per million) of bis-(2-chloroethyl)-sulfide, alkylating agent, in a solvent, dioxane, was added to a 10 ml aqueous solution comprising about $6.5 \times 10^{-5}$ molar alkali metal O-ethyl methylphosphonothioate and permitted to stand for about 7.5 minutes forming an anticholinesterase reaction product. Contacting an enzyme paper including cholinesterase with the anticholinesterase containing aqueous solution at a temperature of about 15° C for about 7.5 minutes in order that the cholinesterase be inhibited by the anticholinesterase with subsequent addition of an indoxyl acetate tablet which is broken followed by shaking and then standing for about 10 minutes. The paper's color remained unchanged thus indicating about 2 ppm of said sulfide was present.

(b) The procedure set forth in (a), supra, was repeated with the substitution for said alkylating agent a member selected from the group consisting of 2,2'-bis-(2''-chloroethylthio)-diethylether, 1,2-bis-(2'-chloroethylthio)ethane, tris (2-chloroethyl)amine, bis-(2-chloroethyl)ethylamine, and bis-(2-chloroethyl)-methylamine forming the corresponding anticholinesterase active compound thus inhibiting the enzyme resulting in no color change of the enzyme paper after contact with the indoxyl acetate tablet.

(c) The procedure in (b), supra, was repeated with the substitution of $3.5 \times 10^{-5}$ molar of O-amyl methylphosphonothioate for the O-ethyl methylphosphonothioate giving rise to similar results.

EXAMPLE 3

(a) An aqueous solution comprising about 25 microliters including about 0.5 parts per million of a mustard which is bis-(2-chloroethyl)-sulfide, 2,2'-bis-(2''-chloroethylthio)-diethylether, 1,2-bis-(2'-chloroethylthio)ethane, tris (2-chloroethyl-amine, bis-(2-chloroethyl)ethylamine or bis-(2-chloroethyl)-methylamine in a solvent, dioxane, and 10 ml aqueous solution comprising about $6.5 \times 10^{-5}$ molar sodium salt of cyclohexylammonium O-ethyl methylphosphonothioate and standing for 15 minutes forming the corresponding anticholinesterase active compound. Contacting an enzyme paper with the solution comprising the anticholinesterase at 35° C for about 15 minutes and then adding the tablet including the indoxyl acetate with shaking the solution with subsequent standing for a time lapse of 15 minutes. The paper's color is unchanged thus indicating the presence of about 0.5 parts per million of the mustard.

(b) The procedure in (a), supra, was repeated with the substitution of $3.5 \times 10^{-5}$ molar of O-amyl methylphosphonothioate for the O-ethyl methylphosphonothioate giving rise to similar results.

Dimethylformamide or dioxane in a concentration up to about $7 \times 10^{-4}$ molar are utilized as solvents. However, the higher concentrations of dioxane which are not preoxide-free may inhibit the enzyme system of the method.

The porous substrate such as Whatman 3MM (available from W. and R. Bolson, Ltd) used in the preparation of the enzyme paper is thick, strong of medium filtering speed with a smooth surface possessing the characteristics of retaining fine precipitates. The enzymes utilized in this invention may be those of mammalian, fish, fowl, amphibian or insect (brain). The more specific cholinesterases are bovine erythrocyte acetylcholinesterase, eel acetylcholinesterase, and horse serum pseudocholinesterase.

The enzyme paper is prepared by first saturating the porous substrate, Whatman 3MM, with the phosphate buffer (0.67M, pH 7.2), allowing to dry and then impregnating the treated paper with the enzyme solution, previously prepared. The papers are dried in a vacuum desiccator. Phosphate buffer (0.67 M, pH 7.2) comprises 7 parts by volume of a solution of 119.0 gm of disodium hydrogen phosphate per liter with 3 parts of a solution of 91.0 gm of potassium dihydrogen phosphate per liter.

An enzyme solution comprising a cholinesterase, bovine erythrocyte acetylcholinesterase, in 5 ml of 0.134 M phosphate buffer, pH 7.2, and 260 mg bovine albumin. The said buffer comprising 7 parts by volume of a solution of 23.8 gm disodium hydrogen phosphate dihydrate per liter and 3 parts of a solution of 18.2 gm potassium dihydrogen phosphate per liter, and other proteins can be substituted for the albumin such as gelatin. The concentration of the enzyme is adjusted to the desired sensitivity.

Each indoxyl acetate tablet weighing 0.5 gm was prepared from a mixture comprising 33.2 gm sodium dihydrogen phosphate dodecahydrate, 10.8 gm potassium dihydrogen phosphate, 2.88 potassium ferrocyanide, 1.80 gm potassium ferricyanide, 1.2 gm indoxyl acetate and 150.12 gm filler (sodium chloride or urea).

We claim:

1. A method of detecting microquantities of nitrogen mustard or sulfur mustard, the steps comprising: adding an unknown solution to an aqueous solution comprising an O-alkyl alkylphosphorothicate salt or an O-alkyl alkylphosphonothicate salt forming a reaction solution, said reaction solution standing for a time sufficient to form anticholinesterase active compound, contacting an inert substrate comprising a cholinesterase with the reaction solution containing the anticholinesterase active compound, said substrate with the anticholinesterase active compound standing for a time sufficient to form an inhibited cholinesterase, adding indoxyl acetate, the absence of color change of the substrate indicates that the unknown solution contains microquantities of the nitrogen mustard or sulfur mustard.

2. A method with claim 1, wherein the standing time is between 7.5 to 15 minutes.

3. A method in accordance with claim 2, wherein the temperature of 15° to 37° C of the reaction solution is maintained during the substrate with the anticholinesterase compound standing time, and observing the non-color change after a time period of 10 to 15 minutes.

4. A method in accordance with claim 1, wherein the acid salts have the formula

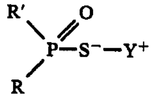

and the anticholinesterase compounds having the formula

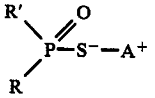

Where:

R is alkoxy group from $C_1$ to $C_5$ carbon atoms

R′ is alkyl group or alkoxy group from $C_1$ to $C_5$ carbon atoms.

Y is:

$Na, K, (Z)_4\overset{+}{N}, (Q)_4\overset{+}{N},$

-continued $(Z_{1-3}—Q_{1-3})_4\overset{+}{N}, (Z_{1-3}—Q_{1-3})—Z—\overset{+}{N}$ or

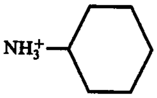

where Z is $C_1$ to $C_4$ carbon atoms, Q is aryl or substituted aryl.

A is: G-S-GCl, -G-S-G-O-G-S- GCl, -G-S-G-S-GCl, $G—N(GCl)_2$, 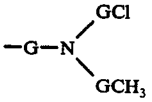 or 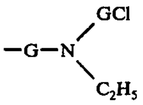

Where G is $—C_2H_4^-$.

5. A member of the group consisting of compounds of the formula

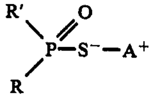

Where:

R is alkoxy group from $C_1$ to $C_5$ carbon atoms.

R′ is alkyl group or alkoxy group from $C_1$ to $C_5$ carbon atoms.

A is: -G-S-GCl, -G-S-G-O-G-S-GCl, -G-S-G-S-GCl, $-G-N(GCl)_2$,

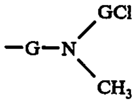 or 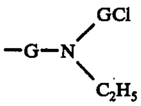

Where G is $—C_2H_4^-$.

* * * * *